United States Patent
Alt et al.

[11] Patent Number: 5,980,566
[45] Date of Patent: Nov. 9, 1999

[54] VASCULAR AND ENDOLUMINAL STENTS WITH IRIDIUM OXIDE COATING

[76] Inventors: Eckhard Alt, Eichendorffstrasse 52, Ottobrunn, Germany, 85521; Lawrence J. Stotts, 327 Linden La., Lake Jackson, Tex. 77566

[21] Appl. No.: 09/059,054

[22] Filed: Apr. 11, 1998

[51] Int. Cl.[6] ....................................................... A61F 2/06
[52] U.S. Cl. .................................. 623/1; 623/12; 604/198
[58] Field of Search ........................... 623/1, 12; 604/198

[56] References Cited

U.S. PATENT DOCUMENTS

| | | | |
|---|---|---|---|
| 5,380,299 | 1/1995 | Fearnot et al. | 604/265 |
| 5,630,839 | 5/1997 | Corbett, III et al. | 607/137 |
| 5,733,326 | 3/1998 | Tomonto et al. | 623/1 |
| 5,800,500 | 9/1998 | Spelman et al. | 607/137 |
| 5,824,045 | 10/1998 | Alt | 623/1 |
| 5,824,049 | 10/1998 | Ragheb et al. | 623/1 |
| 5,824,077 | 10/1998 | Mayer | 623/1 |

*Primary Examiner*—David H. Willse
*Assistant Examiner*—Suzette J. Jackson

[57] ABSTRACT

A vascular stent adapted to be implanted in a blood vessel of a human patient to enhance the flow of blood therethrough, includes an elongate biocompatible metal member of cylindrical shape and tubular sidewall with a pattern of multiple openings therethrough and open ends. The stent has an insertion outer diameter sufficiently small to enable it to be inserted into and advanced through a portion of the vascular system of the body to a preselected point within a coronary artery. The sidewall has a thin adherent coating of iridium oxide covering substantially its entire exposed surface, including the outward-facing surface between openings, the edges of the openings, the inward-facing surface between openings, and the edge of each of the open ends. The coating is of substantially uniform thickness throughout its coverage of the surface of the sidewall, and serves to reduce irritation of tissue of the inner lining of the vessel wall into which the outward-facing surface of the stent comes into contact. The tissue may project as well into the openings in the sidewall to contact the edges thereof. The iridium oxide coating has a biodegradable carrier of drugs applied thereto for beneficial localized action, as by incorporating into the carrier along the inward-facing surface an anticoagulant drug to reduce attachment of thrombi with blood flow through the lumen of the stent. Although it may be composed of multiple layers, the iridium oxide coating is sufficiently thin and flexible to resist flaking during deployment, and the core member has sufficient rigidity when so deployed to resist collapse.

22 Claims, 1 Drawing Sheet

VASCULAR AND ENDOLUMINAL STENTS WITH IRIDIUM OXIDE COATING

BACKGROUND OF THE INVENTION

The present invention relates generally to stents which are implantable or deployable in a vascular or endoluminal location within the body of a patient to maintain the lumen open at that location, and more particularly to improvements in stent coatings.

Stents are expandable prostheses employed to maintain narrow vascular and endoluminal ducts or tracts of the human body open and unoccluded, such as a portion of the lumen of a coronary artery after dilatation of the artery by balloon angioplasty. In the case of an occluded coronary artery, for example, the original blockage is typically attributable to fatty deposits or plaque on the inner lining of the vessel. A different mechanism, however, produces a new blockage after the angioplasty procedure is performed to compress the deposits against the inner lining of the vessel, as by balloon angioplasty, or by removal virtually entirely, using laser angioplasty or rotational cutting. The blood vessel wall is subjected to trauma by any of these procedures, which results in hyperplasia of the neointima, i.e., rapid proliferation of muscle cells in the affected region of the wall, to cause restenosis and re-occlusion of the vessel lumen in a significant percentage of angioplasty patients within a period of from three to six months following the initial procedure.

To avoid this re-occlusion and to maintain the lumen of the vessel open, it is now customary procedure to install a stent at the site in the vessel where the angioplasty was performed. The stent is deployed by radial expansion under pressure exerted by the inflating balloon of a balloon catheter on which the stent is mounted, to engage the inner lining or surface of the vessel wall with sufficient resilience to allow some contraction but also sufficient stiffness to resist to a great degree the natural recoil of the vessel wall that follows its expansion.

The presence of the stent itself in the bloodstream, however, promotes thrombus formation and clotting as blood flows through the vessel. This, too, can result in sufficient blockage of the coronary artery to produce an infarction. Thrombus formation and clotting at the inner lumen of the stent, and fibrosis and restenosis at the site of the vessel wall where the angioplasty was performed and the outer surface of the stent is now engaged, can be significantly reduced by application of appropriate acutely acting drugs in the locality of the stent. Some difficulty is encountered in providing a stent surface which is suitable for retention of the necessary drug(s) to achieve those purposes.

Additionally, it would be desirable to provide a stent with the capability to deliver an effective dose of radiation to tissue at the inner lining of a vessel from which a lesion has been removed or at which a lesion is produced, to further inhibit restenosis at that site. And for purposes of x-ray fluoroscopic viewing of the stent as it is being implanted, as well as examination after the stent delivery system is removed, it is desirable that the stent have a sufficient radiopacity without making its wall so thick that flexibility of the stent and lumen size of the vessel at the implant site are adversely affected.

It is a principal aim of the present invention to provide a stent and method of manufacture thereof which provides a suitable coating on the exposed surfaces of the stent to measurably reduce tissue irritation and, thereby, the traumatic response that produces rapid proliferation of the tissue, as well as to provide improved thrombogenicity, an elongate site for delivery of radiation therapy to irritated tissue, and an improved surface region for carrying an additional biodegradable coating that releases, for example, anti-fibrotic and anti-thrombotic drugs, which also avoids responses tending to initiate a reblockage of the vessel in which the stent is implanted, especially a coronary artery.

Another aim of the invention is to provide a stent with a special coating that resists occlusion of a blood vessel at the implant site attributable to either or both irritation-induced hyperplasia of the intimal and neointimal region of the vessel wall and stent-induced clotting and thrombus formation.

Yet another aim of the invention is to provide a stent which has improved radiopacity for X-ray fluoroscopy viewing without increasing the physical dimensions of the stent.

Still another aim of the invention is to provide a stent with a level of radioactivity sufficient to inhibit cell proliferation at the inner lining of the vessel wall at the implant site, without significant damage to healthy tissue in the vicinity.

SUMMARY OF THE INVENTION

According to the invention, to achieve some of the foregoing aims, the stent is fabricated to have a thin outer coating of iridium oxide. The applicants have found that such a coating is advantageous to reduce adverse tissue reaction to engagement of the stent with the vessel wall at the implant site, and to provide an improved surface for retention of beneficial drugs. In a preferred embodiment, the iridium oxide (sometimes referred to herein as "IROX") layer or film is formed over all exposed surfaces of the stent, so that the IROX-coated outward-facing surface that engages the tissue of the vessel or duct wall when the stent is deployed reduces adverse reaction of the body tissue from contact with the stent. And the IROX-coated inward-facing surface of the stent that defines its lumen is better adapted to provide a suitable support for application of beneficial drugs or other agents that serve to suppress clotting that otherwise arises from the mere presence of the stent in the bloodstream.

A vascular stent is typically constructed from an elongate biocompatible metal member composed, for example, of 316L stainless steel (medical grade), titanium, nitinol (nickel-titanium alloy with shape memory characteristics), iridium, or other metal, which is configured in a cylindrical shape wherein its tubular sidewall is provided with multiple openings therethrough and with open ends. The tubular metal member has an insertion outer diameter sufficiently small to enable the stent to be inserted into and traverse a portion of the vascular system of the body to a preselected point within a coronary artery, for example. According to the invention, the surface of the sidewall is coated with a thin, tightly adherent layer of iridium oxide, preferably with coverage of the entire exposed surface, including the outward-facing surface between the openings in the sidewall, the surface along the edges of the openings in the sidewall, the inward-facing surface between the openings in the sidewall, and the surface along the edge of each of the open ends of the metal member, and is of substantially uniform thickness throughout its coverage.

For deployment, the outer diameter of the stent is expanded or opened by exertion of radial forces outwardly on the sidewall, typically by means of inflating a balloon of a catheter on which the stent is mounted, until the outwardly facing surface(s) of the stent engages tissue of the inner lining of the artery wall at the preselected region where the vessel lumen is to be held open with assistance of the stent. In the case of a coronary artery, for example, this region or location is usually where fatty deposits have been compressed or a lesion has been removed in an angioplasty procedure. Iridium oxide has characteristics of a ceramic material, and, hence, has little flexibility unless it is deposited in a sufficiently thin layer to resist flaking or peeling from the metal base material of the stent, even though it may undergo some fissuring or cracking during deployment. The underlying tubular metal member should possess sufficient mechanical strength to resist collapse under the natural recoil force exerted by the artery wall, when the stent is fully deployed.

In addition, iridium is a noble metal with a high atomic number (Z=77), compared to the atomic numbers of metals of which a stent is typically composed, such as steel (Z=29) or titanium (Z=22), and which have only limited visibility under X-ray fluoroscopy. So iridium provides a much better contrast image or shadow under fluoroscopy when the stent is being implanted in the human body and during any subsequent examination. And since fluoroscopic visibility increases with the third order of magnitude, the same thickness of iridium creates about 5 to 6 times the contrast of a comparable thickness of steel. Thus, a stainless steel stent would require a considerably greater thickness than one having an iridium compound layer, to provide equivalent contrast when viewed by fluoroscope, with resulting disadvantages of reduced flexibility and lumen diameter.

Also, iridium can be converted to a radioactive isotope, $^{192}$Ir, by placement in the neutron efflux of an atomic reactor. The resulting $^{192}$Ir has a half life of 74 days, and emits both beta and gamma radiation. If an iridium oxide coating of approximately five micrometers ($\mu$m, or microns) is applied to a stainless steel core, the absorption of neutrons by the iridium oxide layer is sufficiently high that other radioactive imbalances that might otherwise originate from reactor bombardment of the steel are avoided.

Various coatings have been employed on stents in the past, such as zirconium oxide and zirconium nitride as disclosed in U.S. Pat. No. 5,649,951 to Davidson, and metals from Group VA of the periodic table as disclosed in U.S. Pat. No. 5,607,463 to Schwartz. In general, these coatings have been used to provide tissue compatibility and/or thrombogenicity, but do not offer the many additional advantages of an iridium oxide coating.

BRIEF DESCRIPTION OF THE DRAWINGS

The above and still further aims, objects, features, aspects and attendant advantages of the present invention will become apparent from the following detailed description of a preferred embodiment and process of manufacture thereof constituting the best mode presently contemplated of practicing the invention, when taken in conjunction with the accompanying drawings, in which.

DETAILED DESCRIPTION OF A PREFERRED EMBODIMENT AND METHOD

Figure 1:
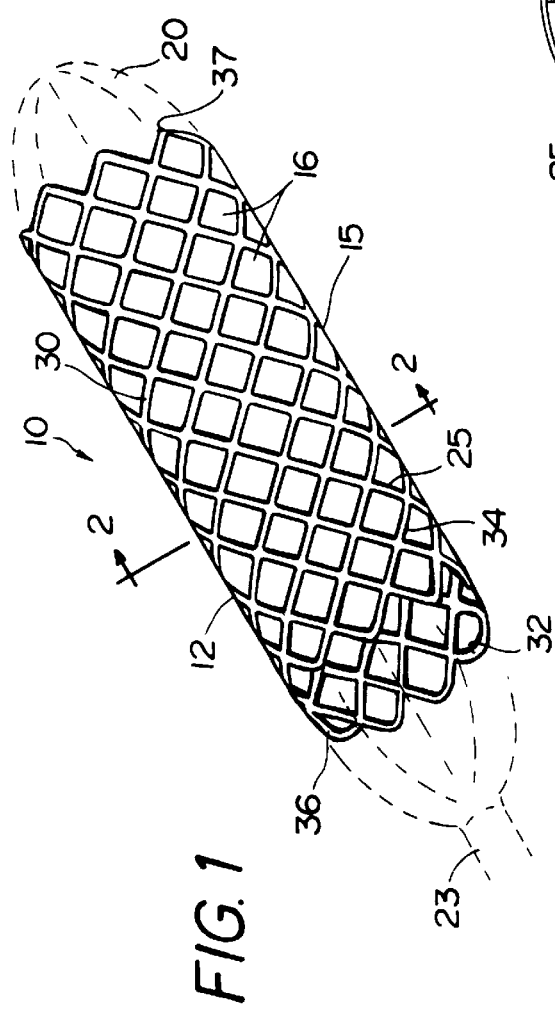
FIG. 1 is a fragmentary perspective view of a vascular or endoluminal stent coated with a thin layer of iridium oxide over its entire surface according to the invention.

In FIG. 1 (the drawings are not intended to be to scale), a stent 10 may be of generally conventional configuration, with cylindrical structure having open ends, and of any known type such as a zig-zag mesh or tube type shown, for example. The material of which the metal member 12 of the stent is composed, i.e., the wire or the solid tube, may be of any conventional and suitable type, such as medical grade 316L stainless steel, chromium, nickel, titanium, iridium or nitinol, for example, which is biologically compatible (biocompatible) with the fluids and tissue of the human body. In any event, the sidewall 15 of member 12 is laced with a multiplicity of openings 16 that extend entirely through the wall. For the mesh type stent, the openings are formed as a natural part of the formation of the mesh itself. For the solid tube type of starting member, the openings are cut in any suitable conventional manner, such as by use of a cutting laser beam. In the latter instance, care must be exercised to prevent the far side (relative to the position of the laser) of the tube from being cut at the same time that the near side cutting pattern is being produced.

The openings 16 should be sized in the usual manner to assure that body fluids (including blood, in the case of a vascular stent) can contact much of the tissue of the inner lining of the wall of a vessel, duct or tract of the human body in which the stent is to be implanted. For vascular stents, it is also important that side branches of vessels should remain open to the main branch of a vessel in which the stent is deployed. Considerations of stent expansion in a relatively symmetrical manner, and the presence of sufficient thickness of metal to provide enough rigidity to resist collapse as the vessel wall exerts its inward pressure during natural recoil when the stent is fully deployed, also play a significant role in determining the size and number of the sidewall openings, as well as the thickness and final configuration of the member 12 itself.

For a stent which is to be implanted in a coronary artery, for example, the outer diameter of the stent resulting from the production process may be in a range from about 1.5 millimeters (mm) to 2.0 mm. In any event, the production diameter (or subsequent compressed diameter) constitutes a first diameter which is sufficiently small to allow the stent to be inserted into the vessel, duct or tract of the body in which it is being used, and to be delivered to the site at which it is to be deployed. At that point, the stent is deployed by inflation of the balloon of a catheter on which it is mounted, to radially expand the diameter to a second diameter which is at least slightly larger than the diameter of the lumen of the vessel, duct or tract at that point. It is common practice to pre-mount stent 10 on a balloon 20 of a balloon catheter 23 (shown in phantom) as a stent delivery system, and to supply the combination in a sterile package for convenience of ready use by the implanting physician. Alternatively, the stent could be mounted on the balloon by the physician at the time the procedure is to be performed.

Again using coronary artery implantation as an example, the mounted stent is inserted into the patient's vascular system at an appropriate location, and is then advanced on the balloon catheter to the selected site. The path of the stent to the site of deployment as well as identification of the target site in the coronary artery are viewed and determined by fluoroscopy. When properly located at the target site, the balloon is inflated by inserting a fluid through an inflation lumen of the catheter to radially expand the stent diameter to an extent that the stent will engage and exert at least slight pressure on the inner lining of the vessel wall. When the stent is fully deployed, the balloon is deflated and the catheter is withdrawn from the patient's vascular system. The stent should possess sufficient mechanical strength in the deployed expanded state to prevent it from collapsing under the radially directed inward pressure exerted by the artery wall as a result of recoil following deflation of the balloon.

When crimped onto the mounting balloon, the coronary artery stent outer diameter will typically lie in a range from about 0.9 to about 1.2 mm, with an inner diameter in a range from about 0.6 to about 0.7 mm. The inner diameter of the stent when fully deployed to the expanded diameter at the target site will typically lie in a range from about 2.5 to about 6.0 mm. The final deployed diameter should be a size which will assure that the stent is retained in place, firmly engaged with the inner lining of the artery wall.

For other vascular sites such as the renal artery, the carotid or femoral artery, or the ductus hepaticus in the liver, a diameter of approximately 4.0 to 8.0 mm is appropriate. This stent size range is produced from tubing of one of the aforementioned core metal materials, typically 316L stainless steel, of 3.2 mm outside diameter and arranged and adapted to be expanded (opened) to a larger outside diameter by cutting a predetermined pattern of openings through the sidewall of the stent. For applications in the bronchial location or in the vascular iliac location, a principal size range of from 8.0 to 12.0 mm outside diameter, fully opened, is desired. For esophageal applications in patients with malignant narrowing of the esophagus lumen, a range of diameter sizes from about 12.0 to 18.0 mm is adequate.

Figure 2:
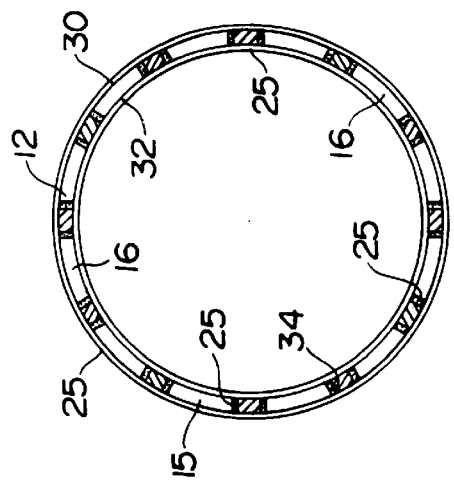
FIG. 2 is a an enlarged cross-sectional view through the line 2—2 of the stent of FIG. 1.

According to the present invention, after production of the stent in the usual manner, and before it is in condition to be mounted on a balloon catheter or other stent delivery system for implantation, it is put through additional production steps in which its exposed surface is coated with a thin adherent single or multiple layer coating 25 (FIGS. 1 and 2), of iridium oxide (IROX). Preferably, this IROX coating is formed in a manner to cover the entire exposed surface of the metal member, including the outward-facing surface 30 and the inward-facing surface 32, as well as the edges 34 of the openings 16, and the edges 36, 37 of the open ends, of sidewall 15.

The coating may, for example, be a single layer or multi-layer produced to a total thickness of about 5 μm to provide better X-ray visualization. For purposes of creating a biocompatible surface alone, however, a thinner coating of less than 900 nanometers (nm), and more preferably a thickness in a range from approximately 10 to approximately 500 nm is sufficient, and most preferably in a range from about 100 to 200 nm. Because of the ceramic-like nature of the iridium oxide coating, a thinner rather than a thicker coating is desirable. Thicker coatings could possibly crack or rupture to an extent that might lead to flaking, shedding or peeling of the coating, whereas the thinner coatings tend to be more flexible, and, although they may undergo some fissuring at the surface when the stent is expanded to the fully deployed state, are considerably less likely to flake, shed or peel.

The bare metal stent may be coated with iridium oxide by any conventional process. Although the invention does not reside in the particular process by which this coating is formed, it is preferred that it result in a coating of substantially uniform thickness (or thinness) on the entire exposed surface (including all edges as well as all side and end surfaces) of the stent core metal. A particularly suitable process, therefore, is one in which a thermal iridium oxide film is produced, which tends to provide more uniform coverage in instances where the configuration of the surface (as in the case of a stent) is not conducive to good overall coverage by sputtering or anodic formation of the film, for example. Nevertheless, one of these latter processes or other process may be employed, with suitable efforts to seek as uniform coverage of the coating as possible.

It is desirable to roughen the surface of the stent in preparation for forming the IROX coating thereon. To that end, the entire surface of the production stent is first etched in a bath of 10% oxalic acid maintained at a temperature of about 100° C., for a period of about 30 minutes. An etch time as short as two minutes in length may be achieved for 316L stainless steel core material, using an aqua regia bath, but care should be exercised to assure that the stents are not over-etched by leaving them in place too long in the bath. The stent is then removed from the bath and thoroughly rinsed in distilled water. Next, the stent is immersed to soak in an iridium solution which has been prepared within the past seven to 14 days, so that all exposed surfaces which are to be coated are contacted by the solution. The iridium solution is prepared by dissolving a mixture of 0.4 gram of iridium chloride to three parts of water in ten milliliters of 20% hydrochloric acid. The solution is heated to evaporate the acid to one-fourth its original volume, and then the original volume of the solution is restored by adding isopropanol. After undergoing the immersion for 16 hours in this solution, the stent is removed, dried thoroughly at room temperature for a period of about one hour, and annealed at a temperature of about 320° C. for a period of about one hour. After each layer is formed, the stent may be subjected to thirty minutes of ultrasonic cleaning in isopropanol The entire process, from immersion to annealing, is then repeated at least once again, except that the anneal step is carried out for a longer period, of, say, from three up to 100 hours on the final layer, to produce on the stent an iridium oxide surface coating in the desired thickness range. From one to four layers have been formed for the overall coating. A plurality of stents may be coated by the process at the same time. As noted above, the resulting coating is stable and sufficiently flexible to resist gross cracking, flaking or rupture, either during compression of the stent when it is being mounted on the balloon catheter, or during expansion of the stent when it is being deployed at the target site, although some surface fissuring may be observed.

Figure 3:
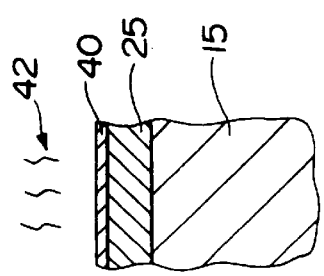
FIG. 3 is a further enlarged fragmentary detailed view of a portion of the cross-sectional view of FIG. 2.

The stent surface is also coated with beneficial drugs which are to be time released to reduce fibrosis and stenosis resulting from an angioplasty procedure and/or from contact of the stent with the inner lining of the vessel wall, and, in use of the stent in a blood vessel, to reduce thrombus attachment and clotting arising from presence of the stent in contact with blood. To that end, the IROX coating of the stent is preferably covered with a biodegradable carrier (such as of a type described in U.S. patent application Ser. No. 08/798,333 of one of the applicants herein), which has the selected drug(s) incorporated therein. This carrier 40 is shown, by way of example, in the fragmentary enlarged cross-section of FIG. 3, overlying at least a portion of IROX coating 25.

Coating 25 may be rendered radioactive (represented by wiggly lines 42 in FIG. 3, for the sake of illustration only) to an activity level suitable to deliver an effective dosage of preferably beta radiation to limited surrounding tissue in the inner lining of the vessel wall to prevent restenosis (or in the case of tumor treatment, a higher dosage effective for that purpose), but with insufficient penetration or level of radioactivity to subject substantial areas of healthy tissue to damage therefrom. This radioactivity level (a predetermined quantity) is achieved by placing the iridium oxide-coated stent in the neutron efflux of an atomic reactor for a period that depends on the output of the reactor, in a conventional manner. The iridium of the coating preferentially absorbs the neutron bombardment, to the lesser, virtual exclusion of the other components of the stent. For this purpose, a thicker IROX coating would be desirable, e.g., 5 $\mu$m, but this must be balanced by the care necessary to assure that the coating thinness is such that it will remain tightly bound to and substantially flex with the underlying core material of the stent during opening of the stent for deployment.

As a practical matter, clinical studies in conjunction with protocols for regulatory approvals to market and use medical devices in general mandate millions of cycles indicative of years of usage, which in the case of stents translates into flexation cycles representative of the nature of the environment of the stent when implanted and in use in the human body.

Iridium oxide has been used in the past as a coating on cardiac pacing electrodes to provide the electrode with low polarization characteristics, and as a material for medical electrodes used in performing certain measurements such as tissue impedances, acidity in the upper gastro-intestinal tract, and variations in blood pH. The applicants, however, are not aware of any use of iridium oxide as a coating to reduce tissue reaction to an implanted prosthesis, or to house a carrier for drugs to provide localized (in contrast to systemic) short-term benefits for retention of a prosthesis in place without ill effects attributable to the human body's natural defense mechanisms, together with advantages of considerably enhanced contrast under x-ray fluoroscopy, and potential application as a radioactive stent for localized radiation to further reduce the possibility of restenosis in use as a vascular stent, or to treat tumors for therapeutic use in duct malignancies. If the stent has been activated with radioactivity, various precautionary safety procedures are mandated to protect service personnel and apparatus from prolonged exposure.

Although a preferred embodiment and method of fabrication have been disclosed herein, it will be recognized by those of ordinary skill in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A vascular stent constructed to be implanted in a blood vessel of a human patient to enhance the flow of blood therethrough, comprising an elongate metal member which is biologically compatible with the blood and tissue of the human body, said metal member having a cylindrical shape to form a tubular sidewall with a multiplicity of openings lying in a predetermined pattern therethrough and with open ends, and having an insertion outer diameter which is sufficiently small to enable the metal member to be inserted into and traverse a portion of the vascular system of the body to a preselected site within a coronary artery, and a thin adherent coating of iridium oxide substantially covering the surface of the tubular sidewall.

2. The vascular stent of claim 1, wherein the iridium oxide coating covers substantially the entire exposed surface of the tubular sidewall, including the outward-facing surface between the openings in the sidewall, the surface along the edges of the openings in the sidewall, the inward-facing surface between the openings in the sidewall, and the surface along the edge of each of the open ends of the metal member.

3. The vascular stent of claim 2, wherein the iridium oxide coating is of substantially uniform thickness throughout its coverage of substantially the entire exposed surface of the tubular sidewall.

4. The vascular stent of claim 3, wherein the iridium oxide coating has a thickness in a range from approximately 10 nanometers to approximately 5 micrometers.

5. The vascular stent of claim 4, wherein said coating thickness is less than 500 nanometers.

6. The vascular stent of claim 2, wherein at least the inward-facing surface is additionally coated with a biodegradable drug carrier.

7. The vascular stent of claim 1, wherein the metal member has an expansion outer diameter to which the stent is selectively deployable by exertion of radial forces outwardly on the tubular sidewall to increase its diameter to said expansion diameter from said insertion diameter, sufficiently to engage tissue of the inner lining of the coronary artery at said preselected site, said iridium oxide coating being sufficiently flexible to resist cracking and separation when said outward radial forces are being exerted to increase the stent diameter, said metal member having sufficient mechanical strength when so deployed to resist collapse under forces exerted by recoil of the coronary artery wall.

8. The vascular stent of claim 7, wherein the iridium oxide coating covers substantially the entire exposed surface of the tubular sidewall, including the outward-facing surface between the openings in the sidewall, the surface along the edges of the openings in the sidewall, the inward-facing surface between the openings in the sidewall and the surface along the edge of each of the open ends of the metal member.

9. The vascular stent of claim 8, wherein the iridium oxide coating is of substantially uniform thickness throughout its coverage of substantially the entire exposed surface of the sidewall.

10. The vascular stent of claim 9, wherein the iridium oxide coating has a thickness in a range from approximately 10 nanometers to approximately 5 microns.

11. The vascular stent of claim 10, wherein said coating thickness is less than about 500 nanometers.

12. The vascular stent of claim 8, wherein the surface of the iridium oxide coating is additionally coated with a biodegradable drug carrier.

13. The vascular stent of claim 1, wherein said iridium oxide coating comprises multiple thin layers of iridium oxide.

14. The vascular stent of claim 1, wherein said iridium oxide coating has a radioactivity level to irradiate tissue adjacent the surface of the stent when implanted in a coronary artery, and sufficient to deliver a radiation dosage which is effective to inhibit stenosis of the inner lining of the artery wall at said preselected site thereof.

15. The vascular stent of claim 8, wherein said iridium oxide coating comprises multiple thin layers of iridium oxide.

16. The vascular stent of claim 8, wherein said iridium oxide coating has a radioactivity level to irradiate tissue adjacent the surface of the stent when implanted in a coronary artery, and sufficient to deliver a radiation dosage which is effective to inhibit stenosis of the inner lining of the artery wall at said preselected site thereof.

17. A vascular or endoluminal stent for deployment in a human body to hold a natural duct or tract thereof open for passage of fluids or solids therethrough, comprising a metal duct or tract of selected length having open ends and a wall laced with openings therethrough and expandable radially from a first diameter smaller than the lumen diameter of the natural duct or tract in which the stent is to be deployed to a second diameter at least slightly larger than said lumen diameter, with sufficient rigidity in its deployed expanded state to resist collapse under radial pressure exerted inwardly on the wall of the stent by the wall of the natural duct or tract in which it is deployed, and a thin coating of iridium oxide on at least the outer surface of the wall of the stent.

18. The vascular or endoluminal stent of claim 17, wherein said coating of iridium oxide also covers the inner surface of the wall of the stent.

19. The vascular or endoluminal stent of claim 18, wherein said coating of iridium oxide is sufficiently flexible to resist flaking and shedding during radial expansion from said first diameter to said second diameter.

20. The vascular or endoluminal stent of claim 17, wherein said iridium oxide coating comprises multiple thin layers of iridium oxide.

21. The vascular or endoluminal stent of claim 17, wherein said iridium oxide coating has a radioactivity level sufficient, when the stent is deployed at the selected site, to deliver a radiation dosage to tissue of the inner lining of the wall of the duct or tract along a preselected region thereof, which is effective to inhibit stenosis thereat.

22. The vascular or endoluminal stent of claim 17, wherein the surface of the iridium oxide coating is additionally coated with a biodegradable drug carrier for timed release of drugs carried within said carrier for localized inhibition of fibrosis and thrombosis.

* * * * *

UNITED STATES PATENT AND TRADEMARK OFFICE
Certificate

Patent No. 5,980,566                                                                       Patented: November 9, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Eckhard Alt, Ottobrunn, Fed. Rep. Germany.

Signed and Sealed this Seventeenth Day of September 2002.

CORRINE M. MCDERMOTT
*Supervisory Patent Examiner*
Art Unit 3738